United States Patent

Jones et al.

[11] Patent Number: 5,869,743
[45] Date of Patent: Feb. 9, 1999

[54] METHOD AND APPARATUS FOR ANALYZING CATALYST AND OTHER SYSTEMS OPERATIONS

[75] Inventors: Barbara L. Jones, King's Lynn; Kenneth W. Peter, Cambs; Marcus J. Hawkins, King's Lynn, all of United Kingdom

[73] Assignee: Sun Electric U.K. Limited, King's Lynn, England

[21] Appl. No.: 797,881

[22] Filed: Feb. 10, 1997

[30] Foreign Application Priority Data

Feb. 9, 1996 [GB] United Kingdom .................... 9602652

[51] Int. Cl.$^6$ ....................................................... F01N 3/20
[52] U.S. Cl. ............................ 73/23.31; 60/276; 123/703
[58] Field of Search .................................... 73/23.31, 116, 73/117.3, 118.1; 60/276, 277; 123/672, 703

[56] References Cited

U.S. PATENT DOCUMENTS

| | | | |
|---|---|---|---|
| 3,926,154 | 12/1975 | Williams | 123/703 |
| 4,194,471 | 3/1980 | Baresel | 123/703 |
| 5,097,700 | 3/1992 | Nakane . | |
| 5,157,921 | 10/1992 | Ito et al. . | |
| 5,175,997 | 1/1993 | Blanke, Sr. . | |
| 5,341,643 | 8/1994 | Hamburg et al. . | |
| 5,357,749 | 10/1994 | Ohsuga et al. | 60/276 |
| 5,360,266 | 11/1994 | Lenfers et al. | 73/23.31 |
| 5,388,454 | 2/1995 | Kuroda et al. . | |
| 5,400,592 | 3/1995 | Mukaihira et al. . | |
| 5,417,061 | 5/1995 | Maeda et al. . | |
| 5,431,012 | 7/1995 | Narula et al. . | |
| 5,444,974 | 8/1995 | Beck et al. . | |
| 5,452,576 | 9/1995 | Hamburg et al. | 60/276 |
| 5,476,001 | 12/1995 | Hoetzel et al. | 73/23.31 |
| 5,487,270 | 1/1996 | Yamashita et al. . | |
| 5,497,618 | 3/1996 | Brailsford et al. . | |
| 5,519,992 | 5/1996 | Hosoya et al. . | |
| 5,526,643 | 6/1996 | Mukaihira et al. . | |

*Primary Examiner*—George M. Dorobroske
*Assistant Examiner*—Eric S. McCall
*Attorney, Agent, or Firm*—Emrich & Dithmar

[57] ABSTRACT

A method of analyzing exhaust gas emissions from an internal combustion engine is modified by the provision of a data process or connected to an exhaust gas analyzer and adapted to monitor changes in exhaust gas concentrations and to identify changes indicative of the state of operation of a catalytic system provided in the engine exhaust delivery system. The catalyst-on condition is identified by reference to the characteristic shape of the plot of the gas concentrations against time. Similar identification of catalyst-off conditions is provided by corresponding analysis of concentration changes and concentration values. The system can distinguish between various causes of the catalyst-off condition.

21 Claims, 8 Drawing Sheets

METHOD AND APPARATUS FOR ANALYZING CATALYST AND OTHER SYSTEMS OPERATIONS

BACKGROUND OF THE INVENTION

1. Field of the Invention

This invention relates to a method and apparatus applicable inter alia to determining catalyst operation in automotive vehicle exhaust systems and applicable to comparable operations for other internal combustion engine systems. A principal application of the invention is to a method and apparatus for use in routine testing of automotive vehicle exhaust gas emissions. In such testing work, the presence of catalytic systems, and the operation of such systems has a direct bearing on the results obtained from such testing work, and there is a need for a more systematic approach to dealing with the variables introduced into such testing work by the presence of catalytic converters.

A broader aspect of the invention relates to the analysis of exhaust gases from an engine system in such a way that transient changes in the concentrations of the exhaust gases are used to provide an indication of the state of operation of the engine and/or its exhaust delivery system including a catalytic converter, if provided.

In automotive applications of the present invention, it will be understood that the method and apparatus will usually find application as part of the routine test equipment employed for analyzing the exhaust gas emissions from such automotive vehicles. The information provided by the method and apparatus of the invention in relation to the operation of a catalytic converter system will usually be used as part of the systematic test work carried out to determine the levels of exhaust gas emissions, and in particular as to whether such emissions meet legislative requirements. The information provided by the method and apparatus of the invention enables a test operation to be carried out with greater certainty and precision. It also enables, in certain cases, a relatively rapid determination to be made that replacement of a catalytic system is required or that associated control equipment such as the so-called lambda sensor or the vehicle's ECU require attention.

2. Description of the Prior Art

Turning to the general background of the invention, it is well known that in response to legislative pressure, catalytic converters are being installed in all new vehicles, at least in certain countries. A catalytic converter however may fail or degrade as a result of age or prolonged usage. Damage arising from failure of another component within the emissions system of the vehicle can also occur. Examples of such related failures are failures of the so-called lambda sensor (which senses the appropriate air/fuel ratio in the engine fuel feed and controls same to ensure proper operation of the catalyst). Another example is the engine electronic control unit (ECU), operation of the engine with leaded fuel or with too lean a fuel mixture, physical shock etc. These factors can all cause total or partial failure of a catalytic converter. Additionally, such converters do not operate at low temperatures i.e., during the first minutes of operation of a vehicle, and neither do they operate in conditions of low exhaust gas flow, e.g., when the engine is idling in heavy traffic.

Accordingly, tests carried out to determine whether a vehicle's exhaust emissions meet legislative requirements need to take into account the state of functionality of the catalytic converter itself and/or its associated control equipment. If, for example, a catalyst fails to turn on (known as "light-off") during emissions testing, as a result of the vehicle not having been warmed up or operated for a sufficient length of time, the vehicle may fail its roadworthiness test. Equally, a catalyst may turn off during testing if the vehicle idles (e.g., at 1K rpm) too long between test phases (e.g., at 2K rpm). A means for automatically indicating catalyst switch-on and/or switch-off would greatly assist in avoiding this problem. Furthermore, a means to detect related partial or complete failures such as those of associated control equipment and an ability to detect and distinguish between such failures and partial or complete failure of the catalyst itself would be an aid to more general diagnostic work.

There is disclosed in U.S. Pat. No. 5,175,997 (Blanke) a feedback control system which analyses three different constituents of the exhaust stream and selectively controls the fuel mixture and air injection of the engine to positively activate and deactivate the catalytic converter, for taking measurements from which the efficiency of the converter can be calculated. The system does not use the gas concentration data to determine the operating state of the converter.

U.S. Pat. No. 5,341,643 (Hamburg) discloses an on-board feedback control system which utilises analysis of plural constituents of the exhaust emissions to control the air/fuel mixture operation of the engine so as to maintain optimum convertor efficiency.

U.S. Pat. Nos. 5,157,921 (Ito) and 5,400,592 (Mukaihira) and 5,417,061 (Maeda) and 5,526,643 (Mukaihira) all disclose on-board systems for detecting deterioration of the catalyst of a catalytic convertor system by means of monitoring concentrations of one or more constituents of the exhaust emissions.

To the best of the Applicants' knowledge a method and apparatus for determining the characteristic shape of the plots of gas concentrations against time of two or more constituents of the gas content of the exhaust output from an internal combustion engine as a means for determining catalyst state of operation, such as catalyst-on or catalyst-off condition, or indeed the analysis of the switch-on and switch-off speeds as a basis for determination of catalyst efficiency and/or remaining life, has not previously been proposed.

SUMMARY OF THE INVENTION

In accordance with the invention a method and apparatus for detecting catalyst state of operation is provided. The system is intended to be utilized primarily during annual road worthiness testing and also for testing for automobile exhausts and catalyst systems during the engine design and development phase, during automotive manufacture and catalyst evaluation, and in the automotive aftermarket.

According to the invention there is provided a method and apparatus for analyzing exhaust gas emissions from an internal combustion engine exhaust delivery system comprising a catalytic system and adapted to provide a signal indicative of catalyzer state of operation.

A supplemental broader aspect of the invention relates to the analysis of exhaust gas concentrations more generally. By monitoring transient concentration changes by means of one or more software algorithms, the system can identify malfunctions such as engine misfires. Accordingly, this supplemental broader aspect of the invention provides a supplemental general diagnostic tool for identification of system functions and malfunctions.

An important sub-aspect of the technique for analyzing exhaust gas emissions relates to the determination of catalyst efficiency and/or catalyst remaining life at the time of testing of a catalytic system. We have discovered that analysis or inspection of the switch-on and switch-off speeds of the catalytic system as determined by the relevant algorithm discussed below reveals information as to the state of efficiency (and thus life left) of the catalyst system. The speeds with which such switch-on and switch-off are effected can be compared to those of base line systems such as brand new catalytic systems, whereby a determination can readily be made of the remaining life of the catalyst, taking account of known profiles for catalytic deterioration during use.

The invention may be used in connection with currently available gas analyzer apparatus employed in automotive exhaust emission test routines which provides data which is conventionally displayed or printed out in digital form indicative of actual gas concentrations as determined by the apparatus for the purpose of the test concerned. The present invention is intended to provide a method and apparatus which can enable such gas concentrations to be determined on the basis of a sure knowledge of the state of operation of the catalytic system. For example when a catalytic system is employed, it is important to know that the catalytic system is clearly in a light-off condition, or else that the catalytic system is partially or completely inoperative due to its own failure, or failure of an associated control system, or else is not hot enough to switch on.

By providing data processing means coupled to a gas analyzer and adapted to determine gas concentrations and/or the rate of change of concentrations of gas analyzed, and/or the pattern of such change, there is provided a means for readily determining whether the catalyst is in its on or off condition at any given time and/or to have some indications of the cause of an off condition.

We have provided, in accordance with the present invention, data processing means employing one or more data processing algorithms which firstly can identify a time instant or period at which the rate of change of concentrations for some or all of the gases monitored in the exhaust gas system, change in accordance with a predetermined pattern or rate or configuration characteristic of catalyst "light-off". By recognizing such a "signature" in the pattern of exhaust gas emissions, and in contrast with the relatively uncharacterized pattern obtained in the absence of an effective catalyzer system, the invention is able to positively and clearly identify when the catalyzer has reached its "light-off" condition and thus when it is appropriate to take definitive emission readings. Secondly, the algorithms can detect gas concentrations and concentration changes indicative of various states of catalyst operation/partial operation/non-operation due to various causes as mentioned above.

There are described below, and illustrated in the accompanying drawings, the actual patterns or signatures obtained in representative test work on particular engines. These patterns all generally follow the representative pattern shown in FIG. 2 of the drawings, though with certain particular variations from this. Accordingly, clear and positive identification of the catalyst "light-off" point is more readily obtained where the test procedure commences from a cold engine and the system can monitor the several characteristic changes in the plot of gas concentration against time, for each of the relevant gases, in order to locate the region at which catalyst "light-off" has occurred. However the relatively warm engine and in such a case it may be sufficient to identify merely the dip in the concentration of hydrocarbon or carbon monoxide or oxygen, which appears in the form of a "knee" in the plot of concentration against time. Likewise, the corresponding small uplift in the plot in the concentration of carbon dioxide at a similar point in the catalyst's cycle is also indicative of catalyst "light-off". It is better to monitor 2 or 3 of the gases.

An important aspect of the invention arising from the graphical analysis of the rates of gas concentration change concerns the ability to determine the efficiency of the catalyst system, and/or the remaining life of it. This is based on the unexpected discovery that the rates of switch-on and/or switch-off of a catalyst system are themselves related to the efficiency and remaining life of the catalyst. Accordingly, we have been able to provide a system for exhaust gas analysis in which there are provided systems for monitoring gas concentration to enable concentration change profiles to be monitored whereby identification of catalyst switch-on and switch-off is achievable. Moreover, as a further step associated with identification of the switch-on or switch-off stage, the time-based analysis of the switching step enables a valid determination to be made of the efficiency and/or remaining life of the catalytic system, particularly where data is available for analysis on a comparative basis with brand new catalyst systems or such systems of otherwise known performance.

BRIEF DESCRIPTION OF THE DRAWINGS

Embodiments of the invention will now be described by way of example with reference to the accompanying drawings in which.

DESCRIPTION OF THE PREFERRED EMBODIMENT

Figure 1:
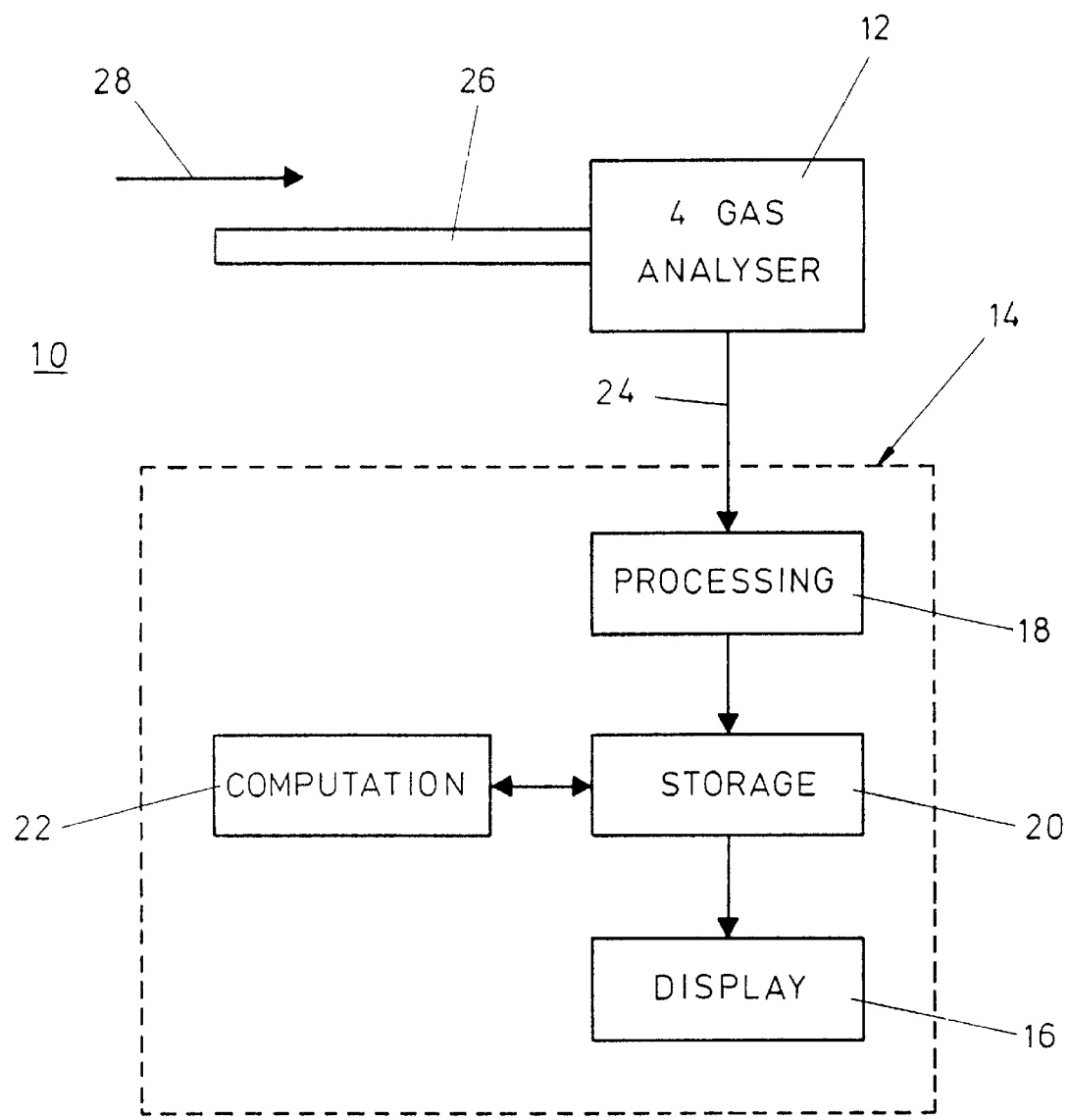
FIG. 1 shows in block diagram form apparatus in accordance with the present invention for analyzing exhaust gas emissions from an automotive internal combustion engine.

As shown in FIG. 1, apparatus 10 for analyzing exhaust gas emissions from an automotive internal combustion engine (not shown) comprises gas analysis apparatus 12 adapted to analyze the concentrations of four gases in the exhaust emissions from the engine, namely hydrocarbons, oxygen, carbon monoxide and carbon dioxide.

Connected to analysis apparatus 12 is data processing apparatus 14 adapted to sample data from analysis apparatus 12 and determine the rate of change of the individual gas concentrations with time and to identify a time instant or period at which the rate of change of concentrations changes in accordance with a predetermined pattern or rate characteristic of catalyst "light-off". The data processing apparatus also includes a display 16 capable of providing a signal indicative of catalyzer "light-off" or otherwise accordingly.

More specifically, data processing apparatus 14 further comprises a data-processing function 18, a data-storage function 20, a computation function 22 and display function 16.

Gas analyzer 12 may be of known form and therefore is not described in technical detail, except to say that, in this embodiment it comprises systems for determining the concentration of four gases, namely carbon monoxide, carbon dioxide, oxygen and hydrocarbons. The data from gas analyzer 12 is passed at 24 to data processing apparatus 14 where the analogue signals are converted to digital form and processed in accordance with the systems described below.

Gas analyzer 12 comprises a projecting probe 26 for insertion into the delivery end of the automotive engine exhaust gas delivery system which delivers exhaust gas in the direction indicated by arrow 28.

Broadly, the system operates as follows. The engine is started from cold. The test itself takes a period of at least 10 or 15 minutes. During this period, the gas analysis apparatus 12 delivers data to the data processing apparatus 14, which processes the data in accordance with the principles described below.

In this embodiment, the processing, storage, computation and display functions 14, 20, 22 and 16 respectively are provided by a personal computer with computation implemented in software and with communication of the data from analyzer 12 via an RS-232 (communication protocol) interface cable to the PC. Alternatively, the implementation of the functions 14, 16, 20 and 22 may be by a dedicated system constructed around a microcontroller with the computation implemented in hardware.

The processing, storage, computation and display functions serve to analyze the incoming data from analyzer 12 so as to determine (without the need to make a physical plot thereof) a computation of the rate of change of gas concentration with time. Effectively therefore the data is processed, for each of the gases concerned, so as to determine the slope of the plot of concentration against time, at any given point in the test procedure.

We have found that as analysis of exhaust gases proceeds from an engine-cold to engine warm or hot condition, the exhaust gases go through three distinct phases, namely:

a) engine start/switch-on stage;
b) catalyst warming stage; and
c) catalyst on or "light-off" phase.

Figure 2:
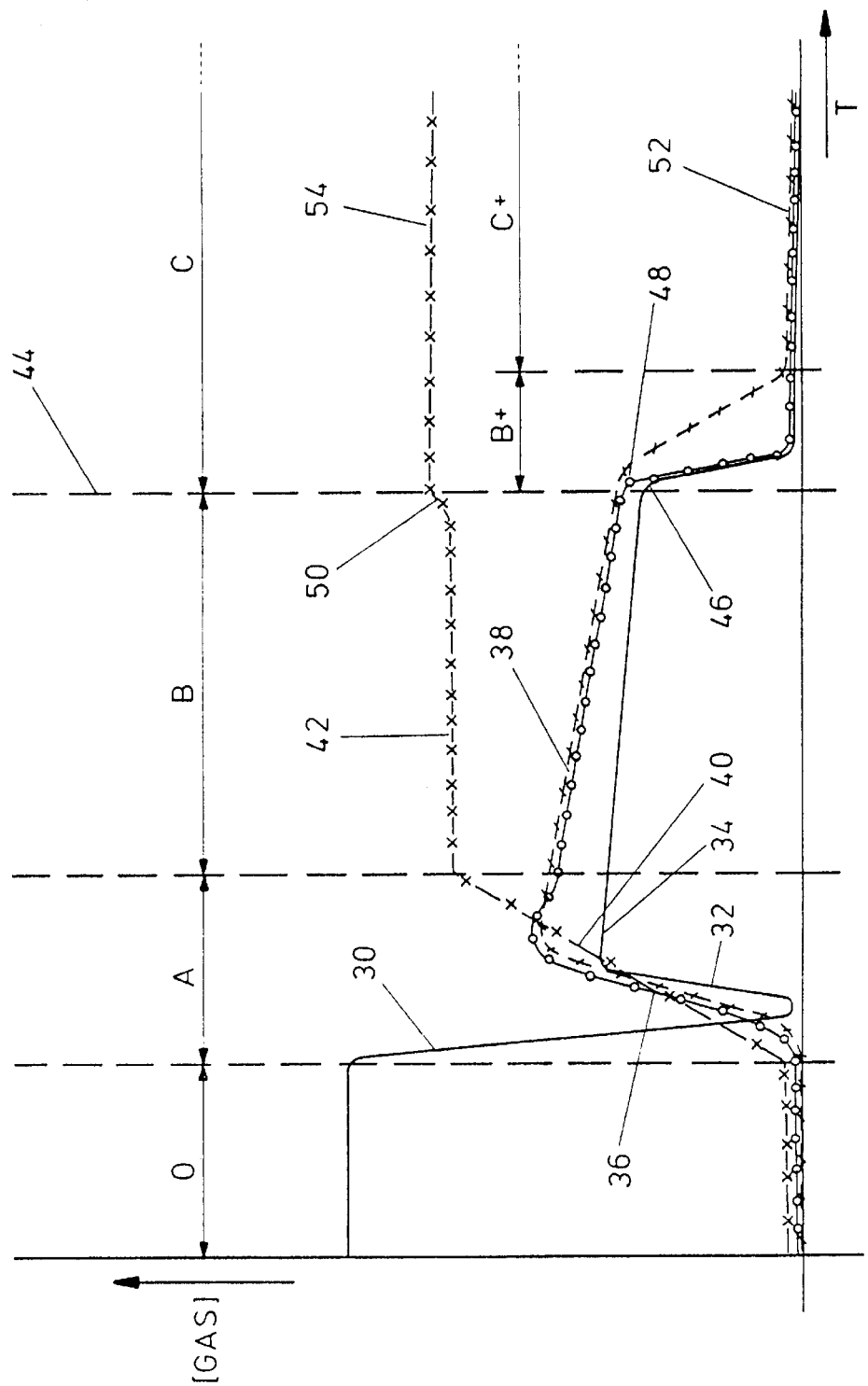
FIG. 2 shows in demonstration format the typical plot of concentration against time for an automotive exhaust system employing a catalytic converter, and including plots for hydrocarbons, carbon monoxide, carbon dioxide and oxygen.

These phases are illustrated in FIG. 2 of the drawings in which gas concentration is plotted against time and the above phases are identified as time bands accordingly. In FIG. 2 there has also been shown the preliminary phase of "engine off" identified as "O".

Thus, in the formalized plot of FIG. 2, in phase "O" with the engine off, the concentrations of the gases (HC and CO and $CO_2$ and $O_2$) are at the values indicated corresponding to substantially zero except in the case of oxygen, which is at its normal atmospheric level.

In the engine start phase, the oxygen level dips sharply at 30, rises likewise sharply at 32 and then plateaus and commences a gentle decrease at 34.

Hydrocarbons and carbon monoxide increase at 36, then plateau and commence a corresponding shallow decline at 38.

Carbon dioxide likewise rises at 40 to a generally horizontal plateau 42.

The plateaus 34, 38 and 42, for oxygen and carbon monoxide and hydrocarbons, and carbon dioxide respectively, all extend across the catalyst warming phase identified at B in FIG. 2.

Finally, each plot undergoes at the interface between phases B and C a sudden increase in the rate of change at the commencement of catalyst light-off or switch-on. This occurs at the interface 44, or thereabouts. This region of change may be identified as a distinct phase or stage and is designated "B+" in examples described below. The changes in gradient are indicated at 46, 48 and 50. The concentrations then settle down to corresponding plateaus at 52 and 54 (carbon monoxide, hydrocarbons and oxygen on the one hand, and carbon dioxide on the other).

There is provided in computation function 22 a software-implemented algorithm which is adapted to detect and indicate the changes of slope at 46, 48 and 50 for each of the four cases in question.

The following is a description in pseudo-code, in an abbreviated form, of the catalyst light-off or switch-on detect algorithm: if $$d/dt(CO_{n+1} \text{ and } CO_n) - d/dt(CO_n \text{ and } CO_{n-1}) > A \text{ and } CO<0.5\%$$

and $$d/dt(HC_{n+1} \text{ and } HC_n) - d/dt(HC_n \text{ and } HC_{n-1}) > B \text{ and } HC<50 \text{ ppm}$$

and $$d/dt(O2_{n+1} \text{ and } O2_n) - d/dt(O2_n \text{ and } O2_{n-1}) > C \text{ and } O2<0.5\%$$

and $$d/dt(CO2_{n-1} \text{ and } CO2_n) - d/dt(CO2_n \text{ and } CO2_{n-1}) > D \text{ and } CO2>14.5\%$$

else if $$CO<0.01\% \text{ and } HC<30 \text{ ppm and } O2<0.01\%$$

then

CAT ON else acquire more data.

In the above pseudo code, the terms A, B, C and D are gradient constants dependent upon the vehicle type and catalyst condition.

The subscripts n, n+1 and n−1 refer to a sequence of successive readings of the concentration of the identified gases. The values of 0.5% carbon monoxide and 50 parts per million hydrocarbon and 14.5% carbon dioxide represent threshold values lying between concentration values indicative of catalyst operation and catalyst failure.

Thus, in any given test, the algorithm-implemented initial test procedure monitors the passage of the exhaust gas concentrations through the sinuosities of the paths shown in FIG. 2 and by reference to the (effectively) stored values of the system provided in the algorithms, is able to determine when the system has reached the interface 44 and the plateaus at 52 and 54, whereupon a signal can be triggered to indicate that the catalyst is "on".

In the event that, for whatever reason, this final stage is not reached, then a corresponding failure signal can be activated after a short time interval corresponding to the maximum time required for the system to reach interface 44.

Turning now to the examples given in FIGS. 3 onwards, these will be related to the theoretical indication in FIG. 2, as follows.

Figure 3:
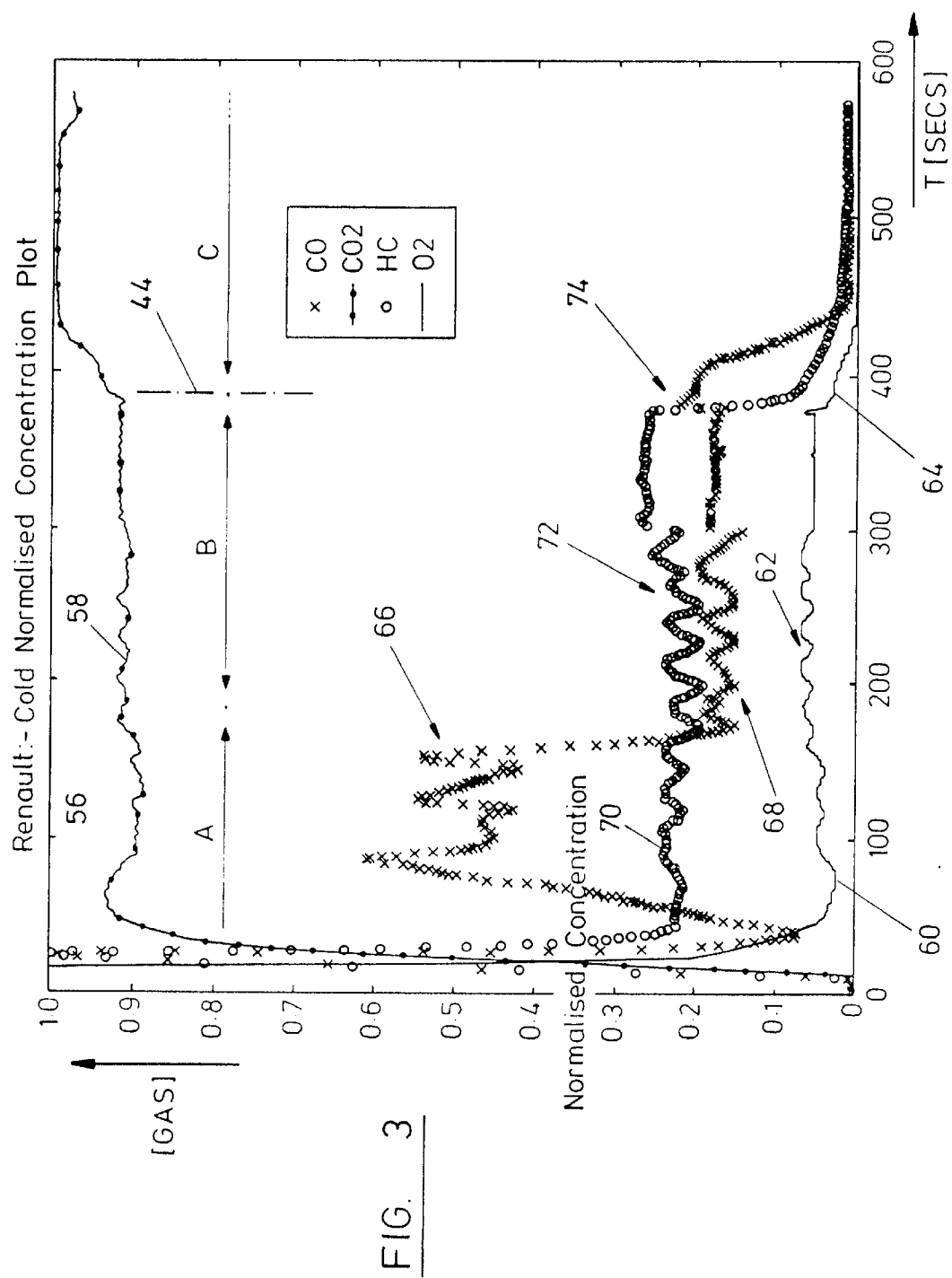
FIG. 3 shows an actual plot, corresponding to that of FIG. 2, for a first test engine, running from cold.

In FIG. 3, the time units are seconds and this plot shows gas concentrations for a Renault engine run from cold.

In the engine start phase "A" which lasts from 0 to 180 seconds, the carbon dioxide concentration characteristically climbs to a peak or maximum at 56 and then stabilizes, more or less in a plateau 58 corresponding to plateau 42.

Oxygen concentration falls to a minimum at 60 and then rises to a somewhat plateau-like region 62, finally falling at 64.

Carbon monoxide produces an eccentric and anomalous peak at 66, which is ignored, followed by a generally undulating region 68 whose average value corresponds generally to a plateau analogous to the plateau 34 in FIG. 2. The hydrocarbon plot 70 has a similar region 72. This latter region is followed by a sudden discontinuity at 74 indicative of catalyst light-off and thus identifying the interface 44 as discussed above in relation to FIG. 2.

Figure 4:
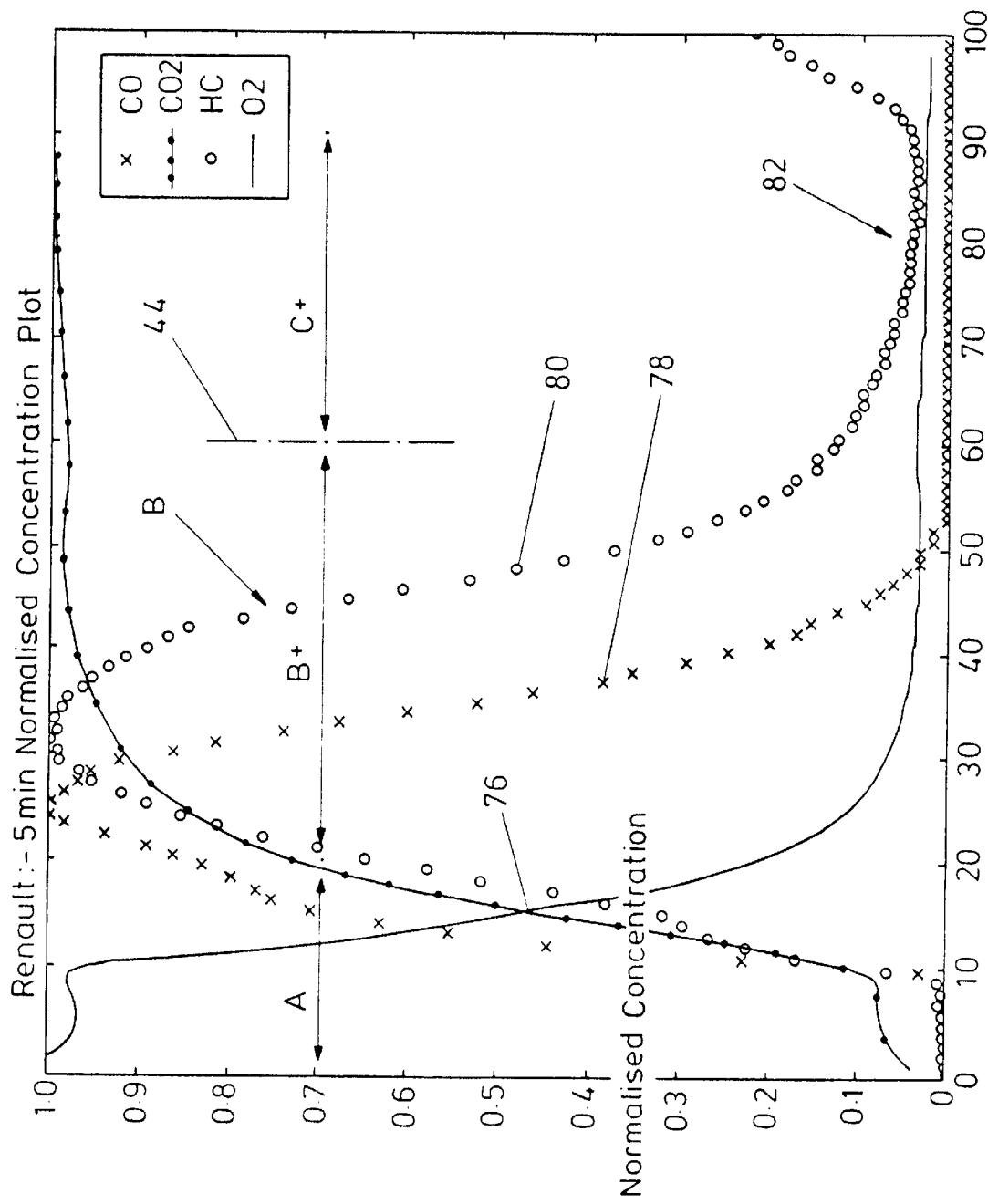
FIG. 4 shows a corresponding plot for the same engine as FIG. 3, but running from a hot condition.

In FIG. 4, the corresponding regions A, B, and C have been likewise identified together with the interface 44.

In the case of FIG. 4, the same Renault engine of FIG. 3 is shown operating from a hot condition in which the engine had been switched off for 5 minutes. In the engine start-up phase, phase A, which lasts from 0 to 20 seconds, oxygen concentration and carbon dioxide concentration characteristically cross over at 76 and carbon monoxide and hydrocarbon concentrations fall rapidly at 78 and 80 to minimum plateau levels indicated at the region 82, corresponding to plateau 52 in FIG. 2.

In this example, the so-called catalyst warming phase "B" from 20 to 60 seconds corresponds in the theoretical plot of FIG. 2, to the region identified at "B+" where the gas concentrations drop from their plateau levels 34, 38 to the level 52. Hence, in FIG. 4 the phase "B" has been shown as such and more correctly identified as B+. The reality of this interpretation is readily explained in view of the fact that the Renault engine in FIG. 4 started from a hot condition after 5 minutes of switch-off. Therefore, a relatively long catalyst warming phase was not required and the oxygen and hydrocarbon and carbon monoxide levels dropped very quickly to their "catalyst on" levels. For conformity with FIG. 2, the "catalyst on" portion of FIG. 4 has been identified as "C+" which in FIG. 2 follows on from the B+ region and corresponds to minimal concentration levels for hydrocarbon and carbon monoxide.

Figure 5:
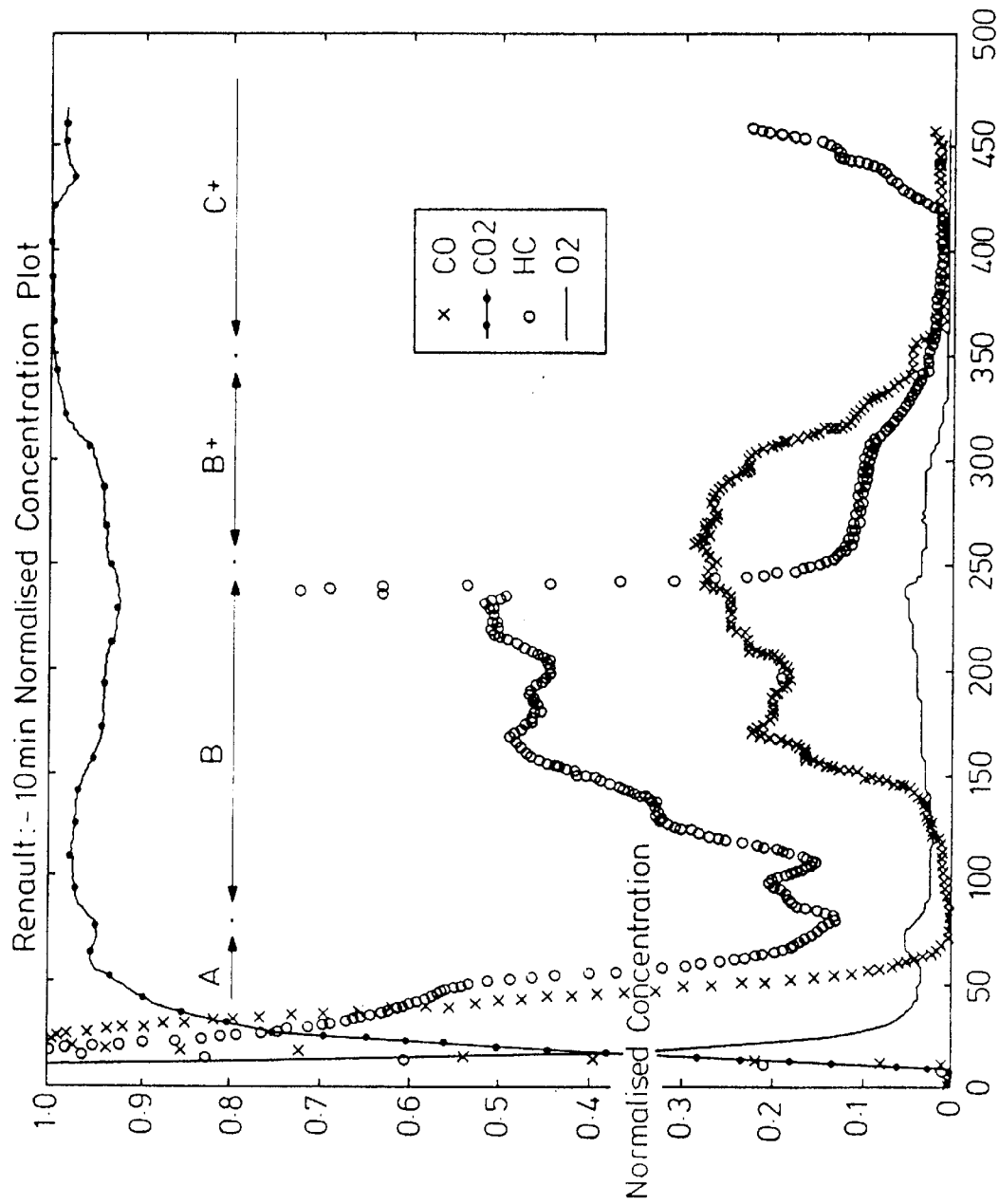
FIG. 5 shows a corresponding plot for the same engine starting from a warm condition.

Likewise, in FIG. 5, the same Renault engine is shown having started from a warm condition (engine switched off for 10 minutes). The phases are, as shown, engine start-up (A=0 to 75 seconds); catalyst warming phase (B from 75 to 250 seconds); catalyst going through light-off phase (B+) 250 to 350 seconds; catalyst on phase (C+) 350 seconds onwards.

Here again, the characteristic profiles of the carbon dioxide and oxygen and carbon monoxide plots can be readily seen. The hydrocarbon plot is a slight aberration of the carbon monoxide plot. Nevertheless, the catalyst light-off phase B+ is readily seen followed by the catalyst-on phase (C+).

Figure 6:
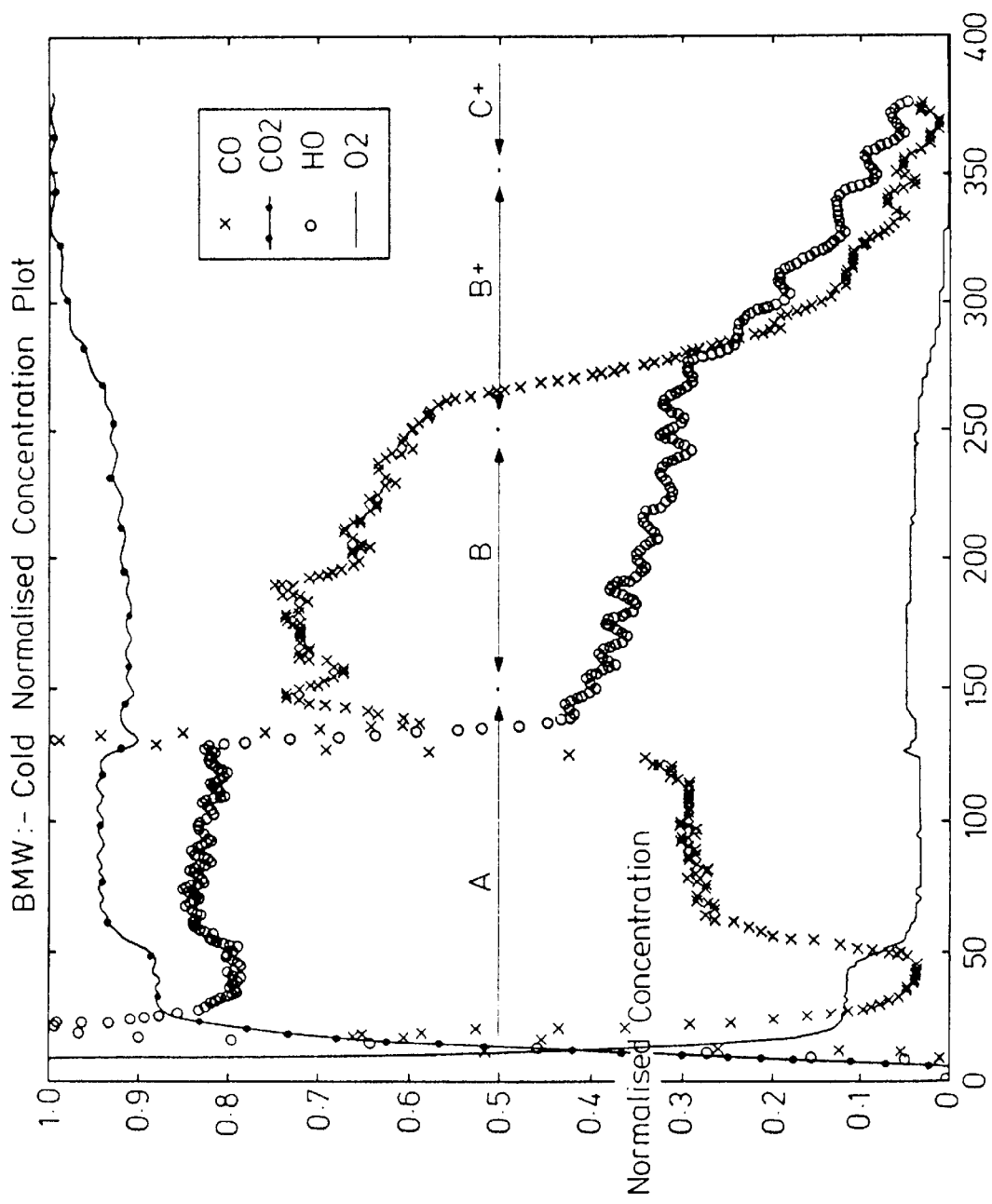
FIG. 6 shows a corresponding plot for a different engine starting from cold.

In the embodiment of FIG. 6, the same phases A, B, B+ and C have been identified for a BMW engine starting from cold. The interpretation of the plots is substantially as discussed above. The phase (B+) of steeply declining carbon monoxide and hydrocarbon concentrations is readily seen, followed by the catalyst-on phase C+.

Figure 7:
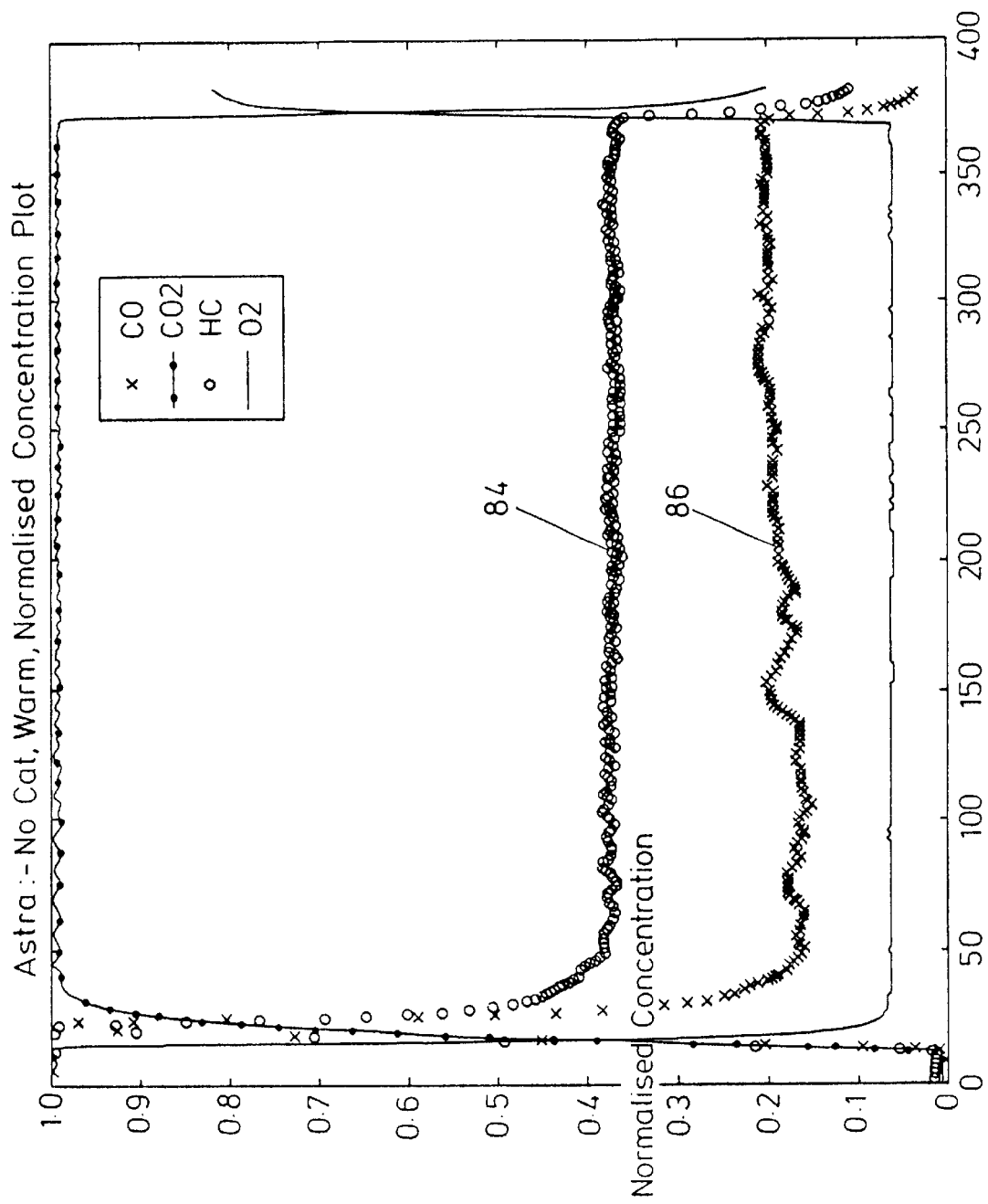
FIG. 7 shows a third engine operating without a catalytic system from cold.
Figure 8:
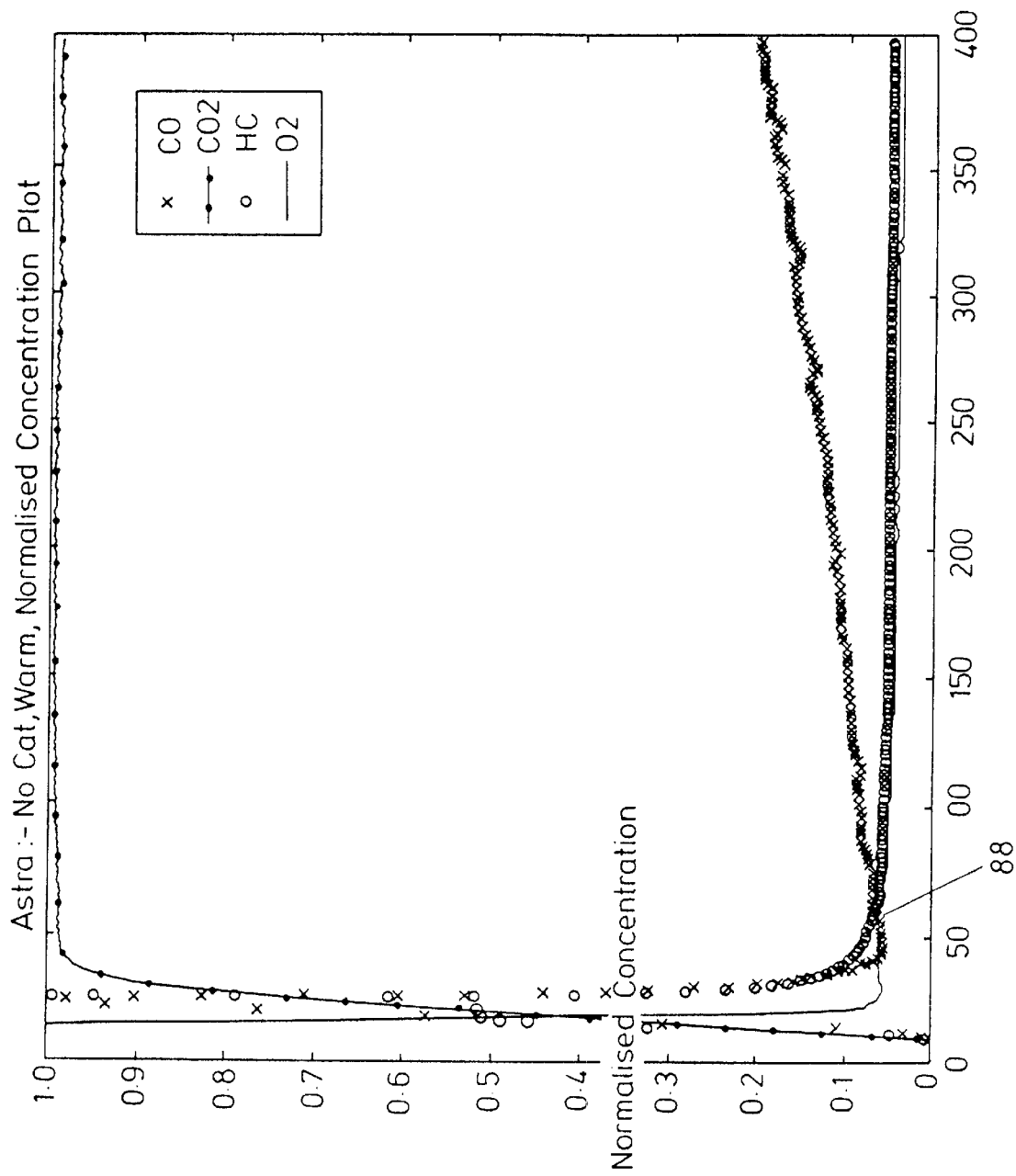
FIG. 8 shows the engine of FIG. 7 running from warm.

The above-discussed examples of the invention are to be contrasted with data set out in FIGS. 7 and 8 which relate to a Vauxhall Astra engine running without a catalyst from cold (7) and from warm (FIG. 8).

As can be seen in FIG. 7, the engine start-up phase from 0 to 50 seconds produces the obvious rise in CO2 and fall in hydrocarbon and carbon monoxide concentrations. Then, the engine warms up and normal running takes place as indicated by the plateaus as 84 and 86. No significant change in direction of the plot can be seen corresponding to those of the catalytic systems of the preceding examples.

In FIG. 8, the same engine is shown running from warm. The general form of the plot is similar to that of FIG. 7. The carbon monoxide concentration is seen to rise from its minimum value at 88. This can be attributed to the slightly different operating conditions. However, in any case the striking differences from those of the preceding examples using catalytic systems is self evident. In the examples, once the algorithm has identified the catalyst-on condition or "light-off" a signal to the user can be readily generated in visual or audible form, whereupon exhaust gas concentration measurements can thereupon be taken for definitive indication of the engine exhaust gas content. Preferably, such indication is provided when the gas concentrations reach the level indicated at "C+", but for some purposes, it will be sufficient to generate the signal after the end of the B phase in FIG. 2 at the interface 44.

In further embodiments, the scope of the gas concentration data analysis is widened from that discussed in the above embodiments (of detecting catalyst switch-on) to detecting other aspects of catalyst operation including switch-off due, for example, to idling the engine too long between successive tests, whereby the catalyst cools. Also, the system is adapted to detect catalytic malfunction due to inherent degradation of the catalyst material as a result of various causes, and/or to detect catalyst malfunction due to partial or complete failure of the associated control systems.

In these embodiments, the data obtained from the gas concentration sensor apparatus is processed by the data analysis system in accordance with a sequence of algorithms adapted to identify the characteristics of each of these catalytic states. Thus, for example, in the case of catalyst switch-off due to catalyst temperature fall, there will be a characteristic increase in concentration of carbon monoxide and hydrocarbons due to the decreased effectiveness of the catalytic material. Such changes are detectable and the algorithm is arranged to trigger a corresponding "switch-off" signal when these reach a threshold value.

Likewise, in the case of a relatively permanent condition of non catalyst operation, unaffected by catalyst temperature, the data-processing system is adapted to recognize the characteristic steady gas concentrations due to an extent of catalyst failure. Moreover, the system can distinguish between such a failure due to, for example, previous use of leaded fuel or sheer passage of time, and a condition caused by a failure of the lambda sensor since, in this latter case, the exhaust gases will show by their concentrations the non-operation or incomplete operation of the mixture-enriching fuel injection step.

We claim:

1. A method of analyzing exhaust gas emissions from an internal combustion engine exhaust delivery system including a catalytic system having a catalyst, said method comprising:

a) sampling exhaust gas delivered by the engine;

b) determining data relating to concentrations of at least three gas components therein;

c) identifying by means of a data-processing algorithm, changes in the concentrations of at least two of the exhaust gas components indicative of switch-on and/or switch-off of the catalytic system;

d) providing a signal indicative of the catalytic system state of operation.

2. A method according to claim 1, wherein the step of identifying includes analyzing rate of catalyst switch-on and/or switch-off as a basis for determining the efficiency and/or the life left of the catalyst.

3. A method according to claim 2, wherein the step of identifying includes comparing said rate of catalyst switch-on and/or switch-off with corresponding baseline data for said systems for said determination of catalyst efficiency and/or life left.

4. A method according to claim 1, wherein the step of identifying includes identifying by means of a data-processing algorithm at a time instant or period at which the rate of change of concentrations for at least two of the gas components in the emissions is in accordance with a pre-determined pattern or rate or configuration characteristic of catalyst switch-on.

5. A method according to claim 1, wherein the step of identifying includes detecting gas concentration changes characteristic of catalytic switch-off due, for example, to engine idling.

6. A method according to claim 1, wherein the step of identifying includes identifying gas concentration changes characteristic of catalytic malfunction, for example due to malfunction of a control system therefor.

7. A method according to claim 2, wherein rate of change of concentration includes a dip in the concentration of at least one gas component selected from the group consisting of hydrocarbons and carbon monoxide and oxygen, such dip producing a "knee" in a plot of concentration against time.

8. A method according to claim 2, wherein the rate of change of concentration includes a small uplift in the concentration of carbon dioxide.

9. A method according to claim 2, wherein the step of identifying a time instant or period includes processing the data on a data-processing system employing an algorithm adapted to monitor the changes of the concentrations and adapted to identify threshold values for the rates of change.

10. A method according to claim 7, wherein the data processing system is adapted to recognize a predetermined pattern or rate or configuration and to generate a corresponding signal accordingly.

11. Apparatus for analyzing exhaust gas emissions from an internal combustion engine exhaust delivery system including a catalyst system having a catalyst, said apparatus comprising:

a) exhaust gas analyzer means adapted to sample exhaust gas delivered by said internal combustion engine; and b) data processing means connected to said exhaust gas analyzer means and adapted to determine data relating to concentrations of at least three gas components in the exhaust gas;

c) said data processing means including means adapted to determine changes in the concentrations of at least two of the exhaust gas components indicative of switch-on and/or switch-off of the catalytic system; and d) said data processing means further including means adapted to provide a signal indicative of the catalyst state.

12. Apparatus according to claim 11, wherein said data processing means includes means adapted to determine the rate of change of the gas concentrations with time and to identify by means of a data-processing algorithm a time instant or period at which the rate of change of concentrations for at least two of the three gas components changes in accordance with a predetermined pattern or rate or configuration characteristic of catalyst switch-on or catalyst switch-off.

13. Apparatus according to claim 11, wherein said data processing means being adapted to analyze rate of catalyst switch-on and/or switch-off as a basis for determining the efficiency and/or the life left of the catalyst.

14. Apparatus according to claim 13, wherein said data processing means being adapted to compare said rate of catalyst switch-on and/or catalyst switch-off with corresponding baseline data for such systems for said determination of catalyst efficiency and/or life left.

15. Apparatus according to claim 11, wherein said data processing means includes means adapted to detect gas concentration changes characteristic of catalytical switch-off due, for example, to engine idling.

16. Apparatus according to claim 11, wherein said data processing means includes means adapted to detect gas concentration changes characteristic of catalytic malfunction due, for example, to malfunction of a control system therefor.

17. Apparatus according to claim 12, wherein said data processing means includes means adapted to identify said time instant or period by reference to a dip in the concentration of at least one gas component selected from the group consisting of hydrocarbons and carbon monoxide and oxygen, such dip producing a "knee" in a plot of such concentration against time.

18. Apparatus according to claim 12, wherein said data processing means includes means adapted to identify said time instant or period by reference to a change in the rate of change of concentration with time comprising a small uplift in the concentration of carbon dioxide.

19. Apparatus according to claim 18, wherein said data processing means includes means adapted to identify said time instant or period by processing said data in accordance with an algorithm adapted to monitor said rates of change of said concentrations and adapted to identify threshold values for said rates of change.

20. A method of analyzing exhaust gas emissions from an internal combustion engine having an exhaust delivery system including a catalytic system, comprising: identifying by means of a data-processing algorithm changes in concentrations of exhaust gas components indicative of switch-on and/or switch-off of the catalytic system to determine state of operation of the engine and/or the exhaust delivery system thereof.

21. A method according to claim 20, wherein the data-processing algorithm is adapted to detect transient changes in the concentrations of exhaust gas components in order to indicate the state of operation of the engine (including malfunctions such as misfires).

* * * * *